United States Patent [19]

Sones et al.

[11] Patent Number: 4,837,686
[45] Date of Patent: Jun. 6, 1989

[54] SUBSTANCE QUANTIFICATION IN ANIMAL BODIES

[75] Inventors: Richard A. Sones, Cleveland Heights; Karen L. Lauro, South Euclid, both of Ohio; Gary T. Barnes, Birmingham, Ala.; Mike M. Tesic, Cleveland, Ohio

[73] Assignee: Picker International, Cleveland, Ohio

[21] Appl. No.: 798,458

[22] Filed: Nov. 15, 1985

[51] Int. Cl.$^4$ ............................................. G01D 18/00
[52] U.S. Cl. .................................. 364/413.19; 378/18
[58] Field of Search .......................... 364/419, 413.19; 378/18, 4, 99; 250/369; 358/111

[56] References Cited

U.S. PATENT DOCUMENTS

| | | | |
|---|---|---|---|
| 4,349,739 | 9/1982 | Annis | 378/99 |
| 4,646,334 | 2/1987 | Zerhouni | 378/18 |
| 4,663,772 | 5/1987 | Mattson et al. | 364/414 X |

OTHER PUBLICATIONS

O'Keefe, M. E., "Calcification in Solitary Nodules of the Lung".
Joseph, P. M., "An Improved Algorithm for Reprojecting Rays Through Pixel Images".
"Principles of Interactive Computer Graphics", McGraw-Hill, pp. 22-25.
Kruger, R. A., "Dual Energy Film Subtraction Technique for Detecting Calcification in Solitary Pulmonary Nodules".
Tarver, R. D., "Experimental Lung Nodule Model: CT Numbers, Nodule Size, and Actual Calcium Content".
Siegelman, S. S., "CT of the Solitary Pulmonary Nodule".

Primary Examiner—Jerry Smith
Assistant Examiner—Charles B. Meyer
Attorney, Agent, or Firm—Watts, Hoffmann, Fisher & Heinke Co.

[57] ABSTRACT

A system and method is disclosed for utilizing image pixel value information generated by a digital radiographic system for quantifying the amount of calcium in a particular object of interest within a subject, wherein the subject also contains additional quantities of calcium located at positions such that the additional calcium interfers with the acquisition of data describing the object of interest. A cursor configured as a parallelogram is described and pixel values are summed along lines parallel to the sides of the parallelogram. A profile is generated from these summations. A portion of the profile corresponding to pixel lines not intersecting the object of interest is used to estimate the contribution of background and other calcium to the profile as a whole, and this estimated value is subtracted from the total profile. Integration of the remainder of the profile provides a scalar value corresponding to the amount of calcium in the object of interest.

36 Claims, 8 Drawing Sheets a) NODULE OVERLAYING RIB.

b) STEP ONE: NODULE REGION.

c) STEP TWO: COMPARISON ("BACKGROUND") REGION.

a)

b)

SUBSTANCE QUANTIFICATION IN ANIMAL BODIES

TECHNICAL FIELD

This invention relates to the field of medical diagnostics, and more particularly to an improved method and apparatus especially suited for use in the environment of digital radiography for employing signals normally used for imaging for quantifying the amount of calcium or other known substance in a particular localized object of interest in a body which contains other sites having the same substance at positions such that the other sites interfere with acquisition of data describing the object of interest.

BACKGROUND ART

Radiography and fluoroscopy are well known diagnostic imaging techniques.

In a conventional radiography system, an x-ray source is actuated to direct a divergent area beam of x-rays through a patient. A cassette containing an x-ray sensitive phosphor screen and light and x-ray sensitive film is positioned in the x-ray path on the side of the patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

In conventional fluoroscopy, a continuous or rapidly pulsed area beam of x-rays is directed through the patient's body. An image intensifier tube is positioned in the path of the beam opposite the source with respect to the patient. The image intensifier tube receives the emergent radiation pattern from the patient, and converts it to a small, brightened visible image at an output face. Either a mirror or closed circuit television system views the output face and produces a dynamic real time visual image, such as on a CRT, for interpretation by a radiologist.

More recently, digital radiography and fluoroscopy techniques have been developed. In digital radiography, the source directs x-radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin fan beam of x-rays is used. In this technique, often called "scan (or slit) projection radiography" (SPR) a fan beam of x-rays is directed through a patient's body. The fan is scanned across the patient, or the patient is movably interposed between the fan beam x-ray source and an array of individual cellular detector segments which are aligned along an arcuate or linear path. Relative movement is effected between the source-detector arrangement and the patient's body, keeping the detector aligned with the beam, such that a large area of the patient's body is scanned by the fan beam of x-rays. Each of the detector segments produces analog signals indicating characteristics of the received x-rays.

These analog signals are digitized and fed to a data processing unit which operates on the data in a predetermined fashion to actuate display apparatus to produce a display image representing the internal structure and/or condition of the patient's body.

One of the advantages of digital radiography and fluoroscopy is that the digital image information generated from the emergent radiation pattern incident on the detector can be processed, more easily than analog data, in various ways to enhance certain aspects of the image, to make the image more readily intelligible and to display a wider range of anatomical attenuation differences.

An important technique for enhancing a digitally represented image is called "energy subtraction".

Energy subtraction exploits energy-related differences in attenuation properties of various types of tissue, such as soft tissue and bone, to derive a material-specific image, mapping substantially only a single material in the body.

It is known that different tissues, such as soft tissue (which is mostly water) and bone, exhibit different characteristics in their capabilities to attenuate x-radiation of differing energy levels.

It is also known that the capability of soft tissue to attenuate x-radiation is less dependent on the x-ray's energy level than is the capability of bone to attenuate x-rays. Soft tissue shows less change in attenuation capability with respect to energy than does bone.

This phenomenon enables performance of energy subtraction. In practicing that technique, pulses of x-rays having alternating higher and lower energy levels are directed through the patient's body. When a lower energy pulse is so generated, the detector and associated digital processing unit cooperate to acquire and store a set of digital data representing the image produced in response to the lower energy pulse. A very short time later, when the higher energy pulse is produced, the detector and digital processing unit again similarly cooperate to acquire and store a set of digital information representing the image produced by the higher energy pulse.

In early energy subtraction techniques, the values obtained representing the lower energy image were then simply subtracted from the values representing the higher energy image.

Since the attenuation of the lower energy x-rays by the soft tissue is about the same as the attenuation of the higher energy x-rays, subtraction of the lower energy image data from the higher energy image data approximately cancels out the information describing the configuration of the soft tissue. When this information has been so cancelled, substantially all that remains in the image is the representation of bone. In this manner, the contrast and visibility of the bone is substantially enhanced by energy subtraction.

Energy subtraction has the advantage of being substantially not subject to motion artifacts resulting from the patient's movement between exposures. The time separating the lower and higher energy image acquisitions is quite short, often less than one sixtieth of a second.

Details of energy subtraction techniques in digital radiography and fluoroscopy are set forth in the following technical publications, all which are hereby incorporated specifically by reference:

Hall, A. L. et al: "Experimental System for Dual Energy Scanned Projection Radiology". *Digital Radiography* proc. of the SPIE 314: 155-159, 1981;

Summer, F. G. et al: "Abdominal Dual Energy Imaging". *Digital Radiography* proc. SPIE 314: 172-174, 1981;

Blank, N. et al: "Dual Energy Radiography: a Preliminary Study". *Digital Radiography* proc. SPIE 314: 181-182, 1981; and Lehman, L. A. et al: "Generalized Image Combinations in Dual kVp Digital Radiography", *Medical Physics* 8: 659-667, 1981.

The above incorporated article by Lehman, et al describes more recently conceived techniques for modifying the above described simple subtraction technique to enhance the quality of the energy subtracted image.

Dual energy subtraction has been accomplished, as noted above, by pulsing an x-ray source in a digital scanning slit device at two kVp's, typically 120 and 80 kVp, and synchronizing the pulses with a rotating filter which hardens the high kVp pulses by filtering out the lower energy x-rays. This results in the patient and x-ray detector sequentially seeing high energy and low energy beams from which the mass per unit area of bone and soft tissue can be solved for.

More recently, it has been proposed in energy subtraction to utilize a particular type of dual energy detector assembly which can produce separate signals representing each of lower and higher x-ray energy incident on the detector. Such a detector assembly enables the practice of energy subtraction without the necessity for switching kVp x-ray output levels, or employing other means for periodically attenuating the x-ray beam, such as rapid interposition and removal of a filter to and from the x-ray path. Such a detector employs a dual layer of phosphor-detector elements, wherein the phosphor material of a first, or front, layer preferentially responds to energy of a relatively lower energy value. A second, or rear, detector layer preferentially responds to x-ray energy in a higher range. Such a detector, and its method of use, is described in published European Patent Application No. 83307157.4 published on Aug. 8, 1984 by Gary T. Barnes, which published application is hereby expressly incorporated by reference.

It is often desirable, in medical diagnostic imaging, to detect characteristics of lesions such as nodules within the human body. Such nodules often are found in the chest area of the patient, including in the lungs. The nodules are typically composed of both soft tissue and calcium, the calcium occurring in differing amounts among different nodules.

The ratio of soft tissue to calcium in a lesion such as a nodule can carry highly significant medical implications. For example, a high degree of calcification of a nodule bears a strong correlation with the likelihood that the nodule is not malignant. Calcification, however, can be an indication of disease other than cancer. Moreover, the progression of calcification often carries significant medical implications as well. Additionally, the relative location of calcification within a nodule can have important significance.

One of the problems in attempting to quantify calcification of a lesion or other structure or object of interest within the body is that normal anatomy includes much calcified structure, such as bone. Additionally, even soft tissue in the body contains trace amounts of calcium which shows up in energy subtraction detection as a measurable background value. Accordingly, a calcified lesion or other structure, whose calcium content is sought to be detected, is almost always overlying or overlain by other interfering calcium, making it difficult to distinguish between the calcium of the lesion or structure sought to be investigated and the other calcium of the body.

A proposal has been made to utilize computerized tomography (CT) equipment for detecting calcification. See Siegelman, S. S., et al., "CT Of The Solitary Pulmonary Nodule", American Journal of Roentgenology, 1980; 135: 1-13; Tarver, R. D. et al., "Experimental Lung Nodule Model: Numbers, Nodule Size, and Actual Calcium Content", Journal of Computer Assisted Tomography, 1983; 7 (3): 402-406.

It is not believed, however, that such methods actually directly determined the quantification of calcification of nodules.

Another proposal involved measuring the difference in optical density on conventional radiographic film exposures between a location within a nodule and a location just outside the nodule, which was said to "allow a quantitative estimate of . . . [calcification] within the nodule." This method, however, yielded only an estimate, and did not directly measure calcification. Also, it was stated to be inapplicable when another calcified structure, such as a rib, overlay the nodule. See Kruger, R. A. et al "Dual Energy Film Subtraction Technique for Detecting Calcification In Solitary Pulmonary Nodules", Radiology, 1981; 140: 213-219.

It is believed that the only known method of directly determining calcification of a nodule, in a practical sense, has been the surgical excision and subsequent chemical assay of the nodule.

It is an object of this invention to provide a non-invasive method and system for accurately determining the quantity of calcium or other substance present in a lesion or structure of an animal body, and to distinguish the substance in the lesion or structure of interest from other presence within the body of the same substance.

DISCLOSURE OF THE INVENTION

The shortcomings of the prior art are eliminated or reduced by use of the present invention, which includes a digital system employing penetrative radiation emergent from a subject to produce pixel values describing a pattern of emergent radiation. The system is adapted to quantify the amount of a predetermined substance located within a localized region of interest within the subject, notwithstanding the subject also contains other sites incorporating additional quantities of the same material, often positioned to at least partially obscure the region of interest.

The system includes means for isolating a first set of pixel values corresponding to a first portion of the pattern which at least partially includes the region of interest. The system also includes means for isolating a second set of pixel values corresponding to a second portion of the emergent pattern which does not include the region of interest. The system further includes means for comparing the respective first and second set of pixel values to derive and produce a scalar indication which is a function of the amount of the predetermined substance located within the region of interest.

Thus, the present invention provides for the noninvasive quantification of the amount of a predetermined substance within a particular region of interest of a subject.

Another aspect of the invention comprises the system being a digital radiography system having imaging capabilities as well. According to the invention, signals generated by the system which are normally employed in its imaging function are utilized, in addition to imaging, for performing substance quantification operation.

According to another specific feature, the digital radiography system includes means for operating in accordance with an energy subtraction mode. Thus, the pixel value signals produced by the system are material specific i.e., they indicate substantially only the distribution within the subject of the predetermined substance of interest.

In accordance with another specific aspect, the system is adapted to provide signals which are specific to the element calcium. Accordingly, the system of this invention can be used to quantify the amount of calcium in a nodule, lesion, or normal anatomical structure, notwithstanding the presence of obscuring calcium in other sites within the subject body.

It is to be emphasized that, while the present invention is discussed, and can be employed, in the environment of an imaging system, the present invention is not, per se, an imaging technique. Rather, signals produced by an imaging system which are normally used to facilitate its imaging function are, according to this invention, employed in other ways to quantify the presence of a particular substance within a known region of interest of the subject. The quantification operation is facilitated by subtracting background and other occurrences of the substance of interest in order to compensate in the final quantification for the response of the system to occurrences of the substance of interest other than in the region of interest sought to be evaluated.

More specifically, the method and system utilize a means which includes means for causing penetrative radiation to pass through a region of the body including the region of interest, and to emerge from the body in a particular pattern describing the tissues it has passed through. The system also includes means for detecting the emergent radiation and, in response to that detection, for generating signals defining a set of image pixel values representing the pattern. The system further comprises means for producing an analog display of the image, and also for producing an image cursor encompassing a portion of the image. The display means includes means for cooperating with the signal generating means for processing separately image pixels located within the region encompassed by the cursor.

One embodiment of this invention includes means for defining a cursor at a first location in the image, the cursor encompassing the nodule or region of interest and a portion of the body component. A cursor is also defined at a second image location not encompassing the nodule or region of interest, but encompassing another portion of the body component. The other portion of the body component encompassed by the cursor at the second location has approximately the same area as the component portion encompassed by the cursor when at the first location.

Prior to cursor definition, the system is actuated to produce and store signals which are subsequently isolated as representing the regions of the image encompassed by each cursor. Each set of signals is separately summed. The sum of the second set of signals is then subtracted from the sum of the first set of signals.

The evaluation is preferably performed by utilization of the system in an energy subtraction mode. When the energy subtraction mode is used, the signals which are stored, subtracted, and whose remainder is reproduced correspond substantially only to the calcium content of the structures within the body, rather than being a result of the attenuation characteristics of all types of materials within the field of view.

In accordance with another specific aspect of the invention, the cursor defines a rectangular configuration.

In another embodiment, the cursor is defined as a parallelogram and has one of its line pairs aligned approximately parallel to an edge of the body component which obscures the nodule or other structure to be quantitatively evaluated.

In accordance with a further specific embodiment, the cursor is defined such that the edge of the component passes through the region encompassed by the cursor.

In another general embodiment, the system described above is also employed. The cursor is defined as a parallelogram which encompasses the nodule and a portion of the obscuring body component, one of the line pairs of the parallelogram being substantially parallel with an edge portion of the calcium-containing body component, with the edge passing through the region defined by the cursor. The cursor defines a region having a dimension along a direction parallel to the body component edge, which dimension is greater than the maximum dimension of the nodule along that direction parallel to the edge.

The system is actuated to produce and store a set of signals representing the pixel values of the image encompassed by the cursor. In a further step, the system sums the pixel values of respective lines of pixels within the cursor. The summations take place in a direction substantially parallel to the sides of the parallelogram as opposed to the line pair which is parallel to the edge of the interfering or obscuring object. A profile is then produced corresponding to these summations. In practice, the profile defines a raised or "hump" portion corresponding to those summed pixel lines which intersect the nodule. Additionally, the profile defines at least one relatively uniform lower "tail" portion which corresponds to summations of pixel lines not intersecting the nodule. The tail portion is interpolated or extrapolated across the rest of the profile to estimate the contribution of background and other calcium to the total profile in the region of the object of interest. The estimates indicated along the profile by the interpolated or extrapolated tail portion of the profile are then respectively subtracted from the corresponding points of the entire profile. The integral of the remaining area under the hump portion of the profile then corresponds to the amount of calcium in the nodule.

This embodiment of the invention enables the noninvasive assay of calcium content in a particular imaged nodule. The cursor need not be moved.

In accordance with a more specific embodiment, the invention is preferably practiced in an energy subtraction protocol.

In accordance with another feature of the invention, the cursor is defined as a parallelogram wherein one line pair of the parallelogram extends substantially parallel to the edge of the body component which intersects the cursor region. The other line pair defining the parallelogram is oriented either parallel or perpendicular to a row of image pixels.

The present invention will be understood in greater detail by reference to the following detailed description, and to the drawings, in which:

BEST MODE FOR CARRYING OUT THE INVENTION

Figure 1:
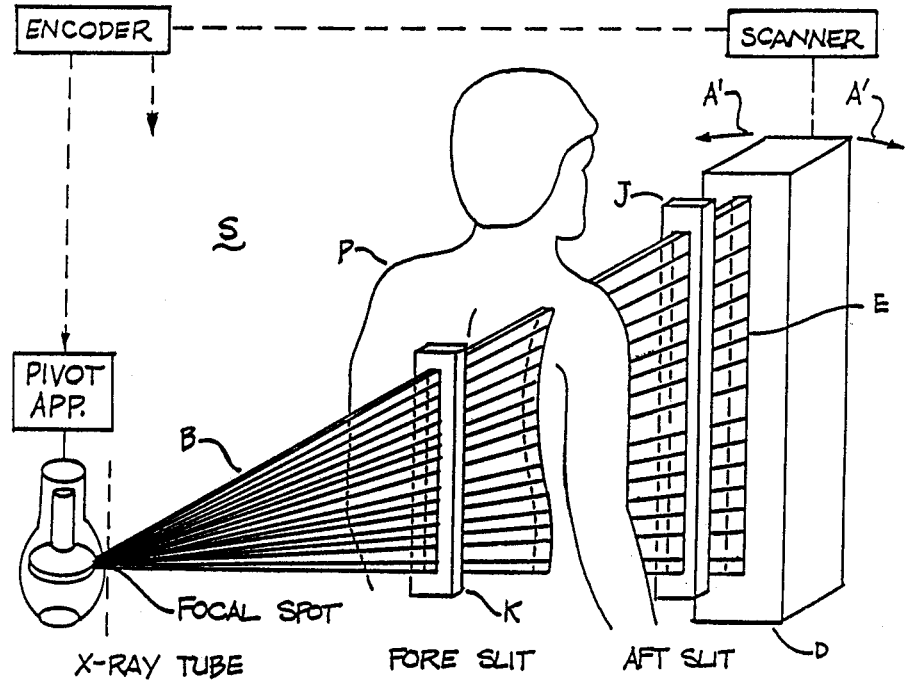
FIG. 1 is a pictorial view illustrating an imaging system in which the present invention is incorporated.
Figure 2:
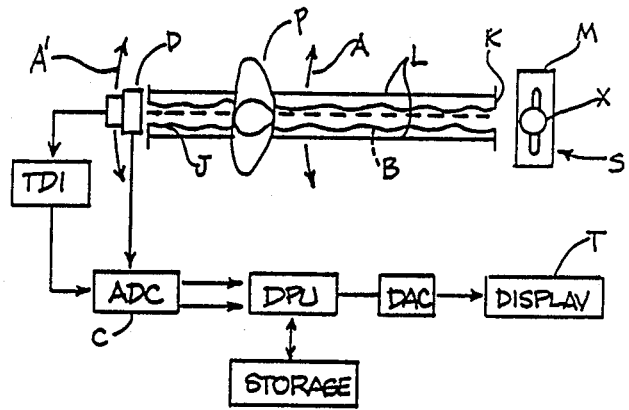
FIG. 2 is a plan view corresponding to the system of FIG. 1.

FIGS. 1 and 2 illustrate a slit projection type of digital radiography system S in which the present invention is incorporated. The system S scans an X-ray spread beam approximately one millimeters in thickness about a vertical axis across a patient's chest and detects a pattern of X-rays emergent from the patient's body. Information represented by the detected X-rays is processed and displayed to illustrate a representation of an image of the patient's internal body structure or condition.

It should be understood at the outset that, while the present invention is described and capable of performance in the environment of digital radiographic imaging systems, the present invention is not in itself an imaging technique. Rather, and as will become clear from the succeeding description, the invention involves method and apparatus for the use and processing of signals which are normally used in imaging to derive and indicate other information relating to quantification of particular materials in certain specified regions of interest within an animal body.

More specifically, the system S includes an X-ray source X affixed to mounting structure M for projecting the spread beam B of X-rays through the body of a patient P, to strike an aligned detector assembly D comprising a plurality of detector elements. The spread beam B is confined by a forward slit K to a substantially vertical plane. The detector assembly D comprises a generally vertically elongated array of individual detector elements V and is aligned with the vertical plane defined by the spread beam B. An aft slit J attached to the detector assembly D serves to further define the spread beam B.

The X-ray source X is mounted on the structure M to rotate about a vertical axis, defined in FIG. 2 as extending into the plane of the paper. Mechanical linkage L couples the X-ray tube X to the detector array D and slits K and J and causes the detector array to scan behind the patient's body along an arcuate path defined by the arrows A, A' in order to maintain the detector assembly D aligned with the beam B throughout the scanning rotative motion of the beam.

The embodiment of the scanning mechanism is not to be limited to fixed or rigid mechanical linkage connecting the elements to be moved. Servo control and associated power drive apparatus embodiments can also be adapted by those of skill in the art to accomplish the desired scanning.

In accordance with another aspect of this embodiment, the X-ray tube X can also be pivoted about its focal spot, to maintain the beam B aligned with the scanning detector.

The X-ray source X is controlled by power means to emit the spread beam B as either a continuous X-ray beam or a rapid succession of X-ray pulses. The X-ray tube X and the detector assembly D synchronously scan, about a vertical axis, across the patient from one side of his body to the other. Analog detector outputs from each of the detector elements are periodically sampled. Each sampling produces analog signals representing a portion of image information. Over the course of the scan from one side to the other side, signals are developed describing a plurality of image lines, which together constitute an area image of the patient's internal body structure.

The analog signals produced by the detector assembly are provided to an analog to digital converter C which digitizes the outputs and feeds them to a digital processing and receiving unit DPU. The DPU processes these digitized output signals to construct a digital representation of an image of the patient's internal body structure scanned by the X-ray beam B, on a pixel-by-pixel basis. Digital signals from the DPU are converted to analog form by way of a digital to analog converter DAC, and fed to a display unit T, which, in response, produces an image in visual form corresponding to the image representing signals from the DPU.

Digital storage means are provided in conjunction with the DPU in order to digitally store the image representations for future use. In such event, the digitally stored signals are later played through the DPU, converted to analog form, and their corresponding images then displayed.

The system S produces at its display an image comprising a rectangular matrix array of individual image pixels. Each pixel is defined by a particular brightness level. The pixels are aligned in respective horizontal rows and vertical columns.

The radiation imaging system generally described above is explained in the following publication by Tesic, M. M., et al., "Digital Radiography of the Chest: Design Features and Considerations For a Prototype Unit", Radiology, Vol. 148 No. 1, pp. 259-264, July, 1983, which is hereby expressly incorporated by reference.

The detector assembly of the system S comprises detector structure such as described in the above incorporated Barnes published European patent application, and in U.S. Pat. application Ser. No. 444,605 filed November 26, 1982 by Gary T. Barnes, also expressly incorporated by reference herein.

More specifically, the detector comprises two generally vertically extending rows of detectors, one behind the other with respect to the x-ray source. Each of the front and rear arrays are disposed along a substantially arcuate path defining a portion of a circle oriented in a vertical plane.

Figure 3:
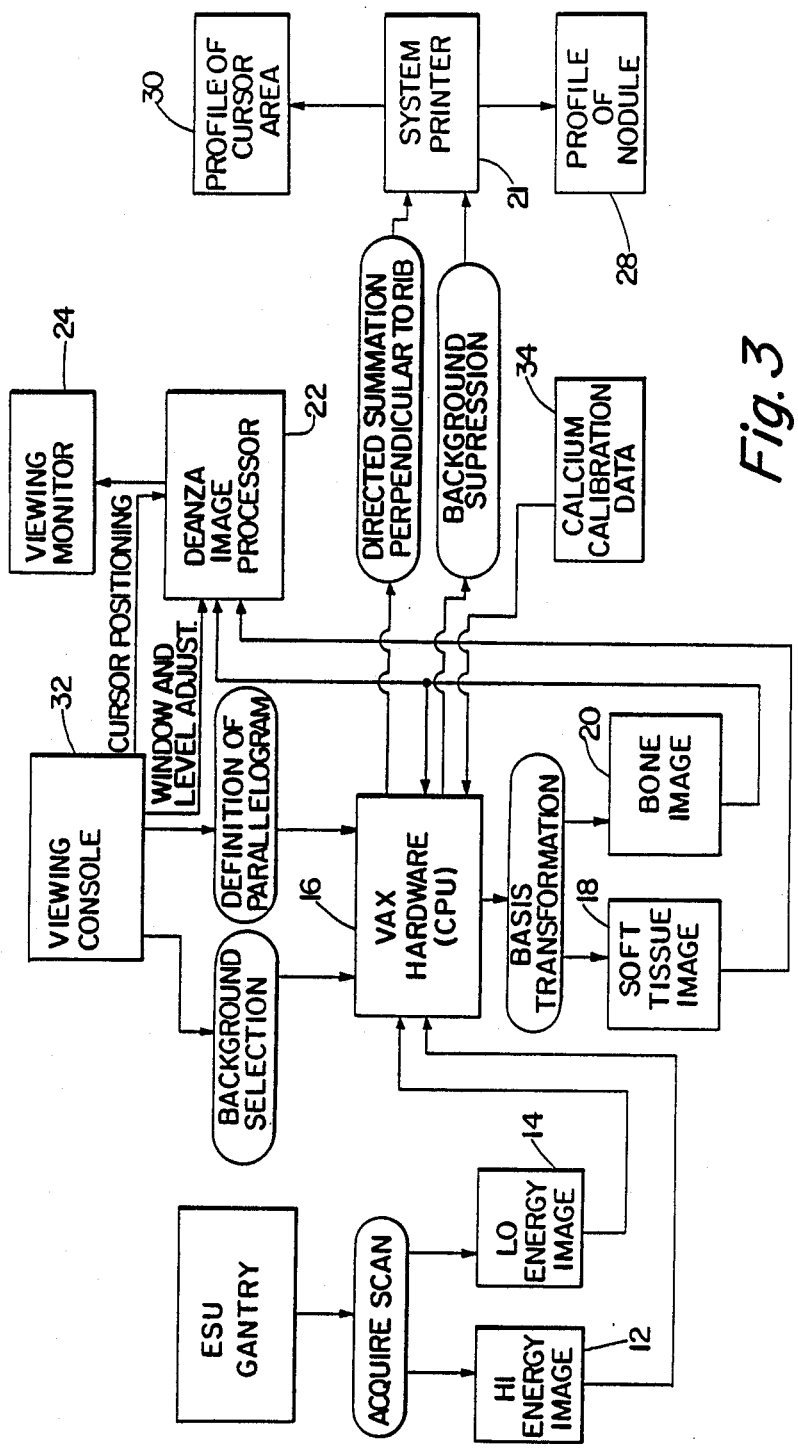
FIG. 3 is a more detailed block diagram illustrating a portion of the system of FIG. 1.

Having discussed the system S in general terms, reference to the block diagram of FIG. 3 describes in more detail the operation of the system.

A block 10 represents the system gantry and its associated dual energy detector. The x-ray source is actuated, and the gantry and detector are caused to move relative to the subject to acquire raw data representing the high energy image 12 and the lower energy image 14. This raw data is fed to a data processing unit 16, which is a VAX 11/750 Processing Unit manufactured by Digital Equipment Corporation, and 2 DEC RM80Disc Drives. The disc drives store the image data to be processed and displayed by the rest of the system. The processing unit services operator requests for specified system functions. Certain computations, to be described in more detail below, are performed here, among which are generation of cursor graphics, execution of reprojection for forward projection operations, and background suppression, discussed in more detail below.

In a known manner, the processing unit 16 produces signals representing a material-specific soft tissue image, indicated at block 18, and signals representing a material-specific bone image, represented at block 20.

The signals representing the respective soft tissue and bone images are transmitted to an image processor 22. The image processor 22 is a Gould DeAnza IP 8400 Image Processor. The image processor 22 manipulates images and graphics for display. Further information on details and operation of the image processor is available in the following publications, each of which is expressly incorporated by reference: Gould DeAnza P8500 Image Processor Software Manual 800219, 1982; and Gould DeAnza IP8500 Image Processor Hardware Reference Manual 800218-REV C, 1983.

An output from the image processor 22 feeds a viewing monitor 24 which produces an analog image corresponding to the processed image data which is manipulated by and output from the image processor 22.

The data processor 16 also produces signals representing certain summations of image pixel data which will be described in more detail below, and which are input to a printer 26. Also input to the printer 26 are background suppression signals. The printer 26 produces tangible representations of summation profiles, indicated at blocks 28, 30. The printer is a DEC LA120 Console/Printer.

The processing unit and image processor receive command instructions from a viewing console unit 32. The viewing console 32 includes a keyboard for typed operator input, and a touch-sensitive plasma panel for information display, control knobs for specifying image window, level and combination angles in known fashion, and a trackball for defining cursor graphics locations. The viewing console also includes three image viewing monitors.

The viewing console transmits image window and level signal controls in known fashion to the image processor 22. The viewing console also transmits to the image processor signals defining image cursor positioning. Image cursor positioning signals are also transmitted to the processing unit 16.

Calcium calibration data are transmitted and processed in known fashion by the processing unit in a known fashion, as indicated at the block 34.

The image processor has, in its commercially available form, inherent cursor creating capabilities. A cursor, for the purposes of this disclosure, means a visible overlay on the image displayed on the analog monitor. The viewing console and image processor identified above also include operator trackball and other controls and circuitry for defining the size, shape and orientation of the cursor. The size, shape and orientation of the cursor are communicated to the processing unit, which includes means for separately processing and handling image representing signals corresponding to the pixels of the image encompassed by the particular cursor selected by the operator. The use of the cursor capability will be discussed in more detail below.

One of the functions of which the processing unit is capable is that of separately summing the brightness values for selected image pixels encompassed by a cursor, either in their entirety, or separately along each of a plurality of separate lines of pixels within the cursor. A known technique for performing this function is known as "reprojection", and is described in the following publication, which is hereby expressly incorporated by reference: Joseph, P. M. "An Improved Algorithm for Reprojecting Rays Through Pixel Images", IEEE *Transactions On Medical Imaging,* Vol. MI-1, No. 3, November, 1982; an alternative technique is described in Newman, W. M., et al., "Principles of Interactive Graphics", 1979, McGraw-Hill, pp. 22–25, also incorporated by reference.

Radiography of the type described above is often employed to search for lesions, such as nodules or other objects of interest in the chest region of a patient to be examined. Such nodules sometimes are benign, but sometimes constitute malignant tumors which must be treated or excised. Such nodules are often calcified to a degree which may vary from one nodule to another. The remainder of the nodule which does not consist of calcium has most of the attributes of soft tissue.

Additionally, bone contains much calcium which is prominently imaged, and even uncalcified soft tissue contains trace amounts of calcium which can show up in radiographic images as measurable background.

Dual energy radiography produces material-specific images of an animal body, and can be set up to map substantially only calcium in the body.

Besides making certain pathological conditions easier to recognize, data describing images derived by energy subtraction techniques are also susceptible of processing to provide quantitative information about the water/calcium make-up of structures or objects of interest such as lung nodules. Such quantification determining techniques provide, essentially, a noninvasive chemical assay of the calcium content of a nodule, other lesion, or of normal anatomy.

Consider an image of bone derived by the use of digital radiography employing the energy subtraction technique. Each pixel of the image defines a ray path from the x-ray tube focal spot through the patient to the detector surface. The value of each pixel is proportional to the amount of calcium along its ray path. In medical physics, it is often convenient to describe the amount (thickness) of a substance being imaged in terms of mass per unit area, usually given as grams per square centimeter ($g/cm^2$). Pixel values in the bone image are proportional to the mass per unit area of overlying calcium.

This technique is described in the following publication which is hereby expressly incorporated by reference: Johns, H. E., et al., "The Physics of Radiology", 4th Edition, 1983, Charles C. Thomas-Publisher, p. 140.

The present invention provides a technique for extracting quantitative data from images of calcium containing nodules, lesions or other body structure as defined by a region of interest. More specifically, the technique is designed to measure the total calcium mass of lung nodules.

Consider imaging a lung nodule. In many cases, the image of the nodule will overlie or be overlain by one or more obscuring interfering objects, such as ribs. For the moment, however, consider the simple case where there is no rib superposition.

The pixel values in the bone image are proportional to overlying or interfering g/cm² of calcium:

$$W = KP \quad (1)$$

where P is a bone image pixel value, W is the g/cm² of calcium overlying that pixel, and K is a constant which is characteristic of the particular imaging system used. Now let $A_p$ be the area (at the image surface) of a pixel, and let M be the nodule magnification. Then the calcium mass $B_j$ overlying pixel j is given by the relation:

$$B_j = (A_p/M^2)W_j = (KA_p/M^2)P_j \quad (2)$$

Assume also, for the moment, that there is no calcium "background" overlying or aligned with the nodule. Then P equals 0 for pixels outside the nodule. Now define a region R which includes the nodule. The total calcium mass B of the nodule is then given by:

$$B = \sum_{j \in R} B_j = (KA_p/M^2) * \sum_{j \in R} P_j \quad (3)$$

Equations (2) and (3) indicate how to calculate the calcium mass of a nodule, assuming: (1) the nodule does not overlie any ribs, and (2) the background overlying and surrounding the nodule has no calcium component.

The two assumptions required, however, to derive equations (2) and (3) are seldom true in practice. The soft tissue background overlying and surrounding a nodule does have a small calcium component. Moreover, tests have suggested that between 50% and 75% of all nodules overlie at least one rib. The term "overlie" as used here means that the shadowgraphic image of the nodule or object of interest is at least partially overlapping with the shadowgraphic image of the other, or interfering, structure, such as a rib as referred to here.

This invention includes a technique for quantifying the amount of calcium in a nodule, lesion or other body structure of interest, while distinguishing the calcium of the structure of interest sought to be evaluated from the calcium background and from the calcium of any overlying ribs or other interfering or obscuring calcium. This technique is illustrated, for example, in FIGS. 4–6.

Figure 4:
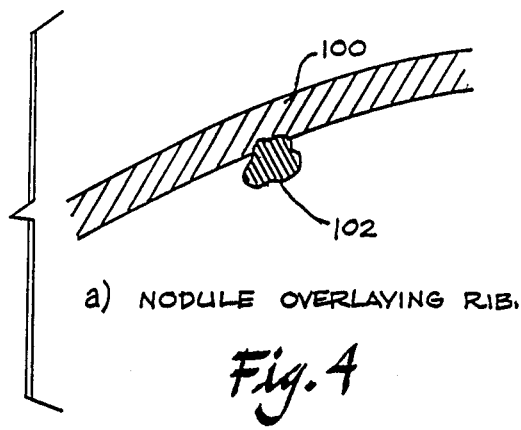
FIG. 4 illustrates a portion of anatomy susceptible of examination by use of the present invention.

FIG. 4 illustrates a portion 100 of a rib of a human patient to be examined, and a nodule 102 partially overlying the rib. As a point of reference, x-rays produced by the system described above are considered as passing through the rib and nodule in a direction perpendicular to the plane of the paper. The detector assembly is not shown.

Figure 5:
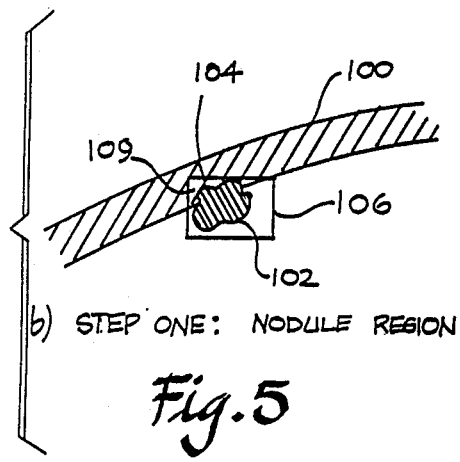
FIGS. 5 and 6 are detail drawings illustrating the application of one embodiment of the present invention.
Figure 6:
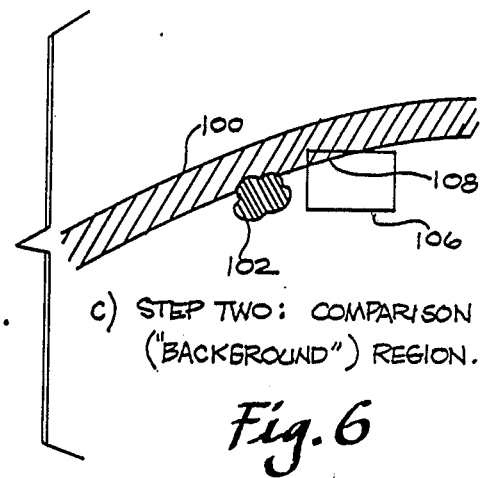

One method of quantifying the calcium in the nodule 102 is illustrated in FIGS. 5 and 6. FIGS. 5 and 6 illustrate the rib 100, the nodule 102, and a rectangular box 106. The box 106 is to be considered as a cursor appearing on the display screen of the main imaging system described above at a location corresponding to its location illustrated in FIGS. 5 and 6, respectively. The cursors' size, orientation, and position are controllable by an operator in known fashion. The purpose of the cursor is to define a region of interest around the nodule. The main imaging system, as noted above, is in known fashion capable of separately processing, enhancing and/or handling data from image pixels within the boundaries of the regions defined by the cursors.

In FIGS. 5 and 6, the cursors are rectangular, having their side pairs aligned in horizontal and vertical directions. The cursors can, however, be of any mutually congruent geometry. The system S is capable of establishing multiple cursors simultaneously, and the cursors illustrated in 5 and 6 are established in that manner.

One method of evaluating the amount of calcium in the nodule 102 is to compare two sets of data, i.e., the data acquired in the region defined by the cursor 106 at the FIG. 5 location, and one set acquired in the region defined by the cursor located as in FIG. 6. This will be described in more detail below.

The cursor of FIG. 5 is established to encompass all of the nodule 102, a portion of the rib, and other background. The cursor of FIG. 6 is established to encompass a portion of the rib, and other background, and does not encompass any portion of the nodule 102. The rib portion 108 defined by the cursor positioned as in FIG. 6 is substantially the same size, shape and location relative to the rib edge as the region 109 of the rib encompassed by the cursor of FIG. 5. Thus, the cursor depicted in FIG. 5 defines a region whose image pixels describe the contribution to radiation attenuation brought about by the relatively uniform soft tissue calcium traced background, by the rib, and by the nodule. The region defined by the cursor as positioned in FIG. 6 exhibits radiation attenuation effects brought about by only the relatively uniform background, and by the rib. Moveover, the portion of the rib included within the cursor of FIG. 6 is substantially congruent, and analogously positioned, as is the rib portion encompassed by the cursor of FIG. 5.

The data acquired from the pixels defined by the two cursors simultaneously positioned as in FIGS. 5 and 6, respectively, are separately stored. The pixel values of the pixels encompassed by the cursor of FIG. 5 are summed. The pixel values encompassed by the cursor positioned as shown in FIG. 6 are separately summed. The sum associated with the cursor of FIG. 6 is subtracted from the sum associated with the cursor of FIG. 5. Where the data from the regions of the two cursors is derived from information describing the calcium image of the subject, as in energy subtraction, the remainder, a scalar number, is a function of the quantity of calcium in the nodule. The subtraction operation effectively cancels out the contribution of calcium located in the rib, and calcium located in soft tissue in the region.

While this embodiment of the invention is primarily described for use in the context of dual energy subtraction, it is contemplated that useful information can be derived by the implementation of this embodiment in the context of single energy exposures. Where only single energy exposure is used, however, the information derived will be a function of the total mass of the nodule, rather than a quantification of its calcium content alone.

Another embodiment of a method for assaying the amount of calcium in a nodule is to derive a "local" background from a region defined by a stationary single cursor.

Such a technique is illustrated in connection with FIGS. 7-9.

Figure 7:
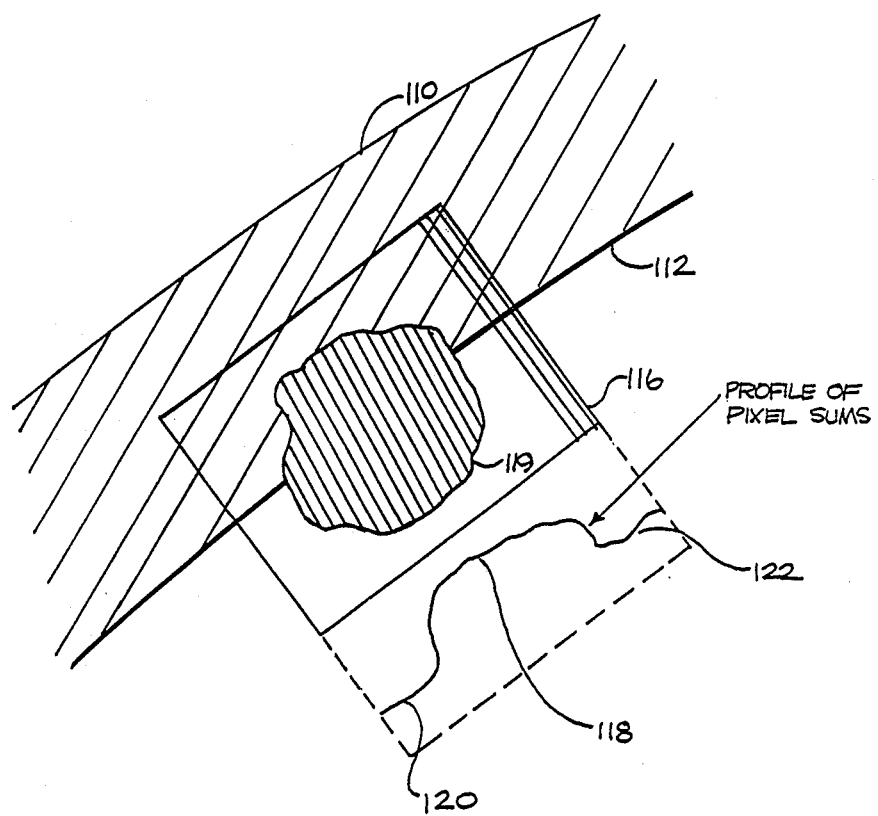
FIGS. 7-9 are detail and graphical drawings illustrating the application of another embodiment of this invention.

FIG. 7 shows a nodule 119 partially overlying a rib 110, and enclosed within a rectangular cursur box 116. As in connection with the previous embodiment, this box is to be thought of as a cursor on a display. The cursor's size, orientation and position are controlled by an operator. The purpose of the cursor is to define a region around the nodule.

In this embodiment of the invention, two assumptions are made about the distribution of calcium in the rib: (1) the rib edge 112 is approximately a straight line over the region defined by the cursor and (2) the rib calcium distribution varies substantially only in the direction perpendicular to the rib edge. It is also assumed that the background soft tissue calcium is essentially constant over the region defined by the cursor.

The cursor rectangle is oriented with one pair of sides parallel to the rib edge. Within the cursor, pixel sums are generated along lines perpendicular to the rib edge, yielding a summation profile of the cursor region. Such a profile is illustrated in FIG. 7, where an elevated portion, or "hump" 118 evidences the calcium in the nodule. The profile also includes "tail" portions 120, 122.

Preferably, the image pixel values are generated in the environment of execution of the energy subtraction technique discussed above, such that the resultant summation profile is based on substantially only data representing the content of calcium in the structures encompassed by the cursor.

This technique could, however, be used with single energy radiography, but the profile would then depict the attenuation characteristics exhibited by all the materials within the cursor-defined region, rather than on the particular attenuation characteristics of the calcium alone.

The hump portion of the profile corresponds to the region in which pixel lines perpendicular to the rib edge intersect the nodule, while the tail portions of the profile correspond to regions within the cursor wherein lines of pixels perpendicular to the rib edge are aligned only with a portion of the rib itself and with background material, and do not intersect the nodule.

Figure 8:
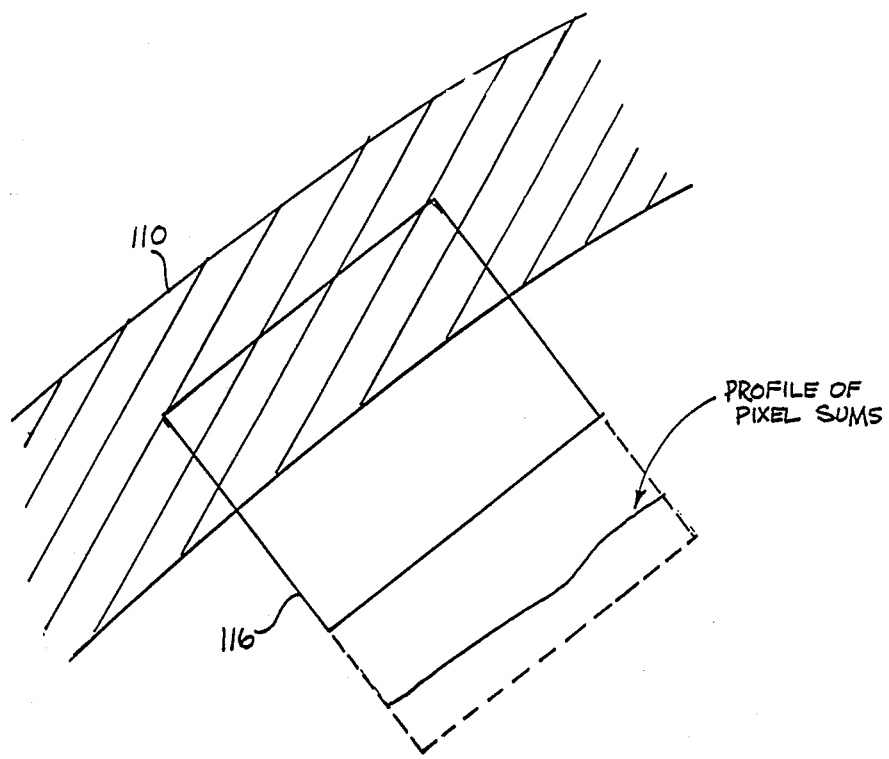
Figure 9:
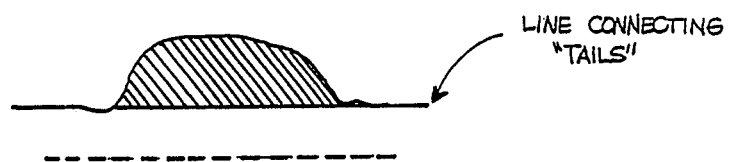

As an aid in understanding how this technique works, consider FIG. 8 which is identical to FIG. 7 except that the nodule is absent. Thus, the profile in FIG. 8 is derived from only the rib configuration and the uniform calcium background contribution, and is thus approximately uniform along a direction parallel to the rib edge. This uniformity results from the rib edge being substantially a straight line and the rib having substantially uniform calcium distribution along a direction parallel to its edge.

In order to obtain a representation which corresponds substantially only to the calcium in the nodule, one simply overlays the profiles of FIGS. 7 and 8 and subtracts away the contribution to the profile of FIG. 7 which results from the rib/background contribution, leaving only the nodule calcium profile. The nodule calcium profile can then be integrated in a known manner to yield a value for total calcium content.

It is important to realize that the procedure depicted in FIG. 8 is not actually separately performed distinct from the procedure depicted in connection with FIG. 7. The FIG. 8 procedure is hypothetical only. In practice, the rib profile (the uniform profile shown in FIG. 8) can often be estimated with sufficient accuracy in the profile of FIG. 7 by simply connecting the tails of the FIG. 7 profile produced by the combination of the rib/background/nodule combination. This procedure is illustrated in FIG. 9, where the shaded area corresponds to the integral of the nodule calcium profile.

Where the two "tail" portions of the summation profile are approximately horizontal and of equal value, interpolation of the value of the rib/background portion (FIG. 8) across the area of the nodule (FIG. 7) comprises only a simple step of connecting the two tail portions over the space between them. Where, however, the respective tail portions are of different magnitudes, or are non-uniform along their visible lengths, known interpolation or extrapolation techniques can be employed to obtain a statistically valid estimate or approximation of the rib/background contribution of the FIG. 8 profile as it affects the nodule encompassing portion of the total profile as shown in FIG. 7.

Where S represents the integral of the nodule calcium profile, S is analogous to the pixel summation of equation (3), so the total calcium of the nodule is given by:

$$B = (KA_p/M^2) \times S \qquad (4)$$

In developing the sums of pixel lines extending perpendicular to the rib edge, it must be kept in mind that, (in the FIG. 7 embodiment) unless the rib edge happens to be aligned with the actual pixel rows or columns in the image produced by the system, means must be employed to approximate the pixel line integrals. Orientation of the cursor at a non-parallel angle with respect to the pixel lines or columns necessitates employment of a known technique called "reprojection". Reprojection sums the pixels encompassed within the non-parallel orientated cursor in a way which causes approximations of pixel lines within the cursor. The pixel sums thus derived are really approximations to line integrals, and so the technique amounts to finding a method for estimating an arbitrarily directed line integral. This problem is generally referred to as reprojection or forward projection because it is, in a sense, the reverse operation of back projection, a known technique often used in computerized tomography. Reprojection techniques suitable for incorporation in the practice of this invention are discussed in the above incorporated articles by Joseph and by Newman.

Another embodiment of the present invention makes it possible to obtain the advantages of the previously described embodiment without the necessity for employing complex, general reprojection techniques in generating pixel line integrals.

Figure 10:
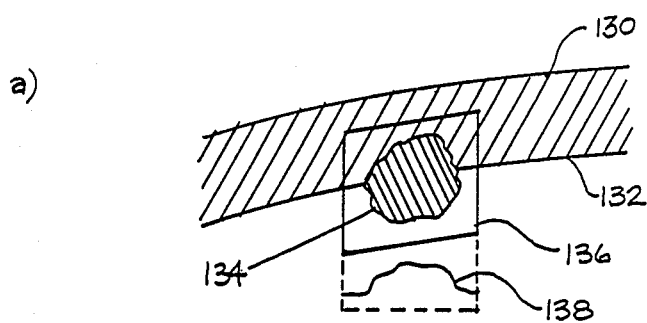
FIGS. 10-14 are detail drawings illustrating the application of additional embodiments of the present invention.

In accordance with this embodiment, and with reference to FIG. 10, a rib 130 having an edge 132, and a nodule 134, are shown. In the embodiment of FIG. 10, however, the cursor is defined as a parallelogram 136.

As in the case of FIGS. 7 and 8, the rib edge 132 is oriented at an angle in the image which is neither vertical nor horizontal, and is thus not parallel to either the columns or rows of pixels.

The parallelogram shaped cursor 136 has no right angles. The parallelogram 136 has one of its side pairs oriented substantially parallel to the rib edge 132, while the other side pair is oriented vertically. This means that, if pixel lines parallel to the vertical side pair are summed across the parallelogram 136, it is not necessary to employ any reprojection techniques, since the summed lines of pixels are parallel to the pixel lines defined in the image detection apparatus. In FIG. 10, a profile 138 is illustrated, which is developed in a manner analogous to that described in connection with FIG. 7. As in the embodiment described in connection with FIGS. 7 and 8, the tail portions of the profile 138 can be connected, and the area of the hump above the connected tail portions represents the total calcium content of the nodule 134.

The embodiment described in connection with FIG. 10 is employed when the slope of the line 132 defined by the rib edge is less than or equal to unity, i.e., when the angle of the line 132 to the horizontal is less than or equal to 45°.

Figure 11:
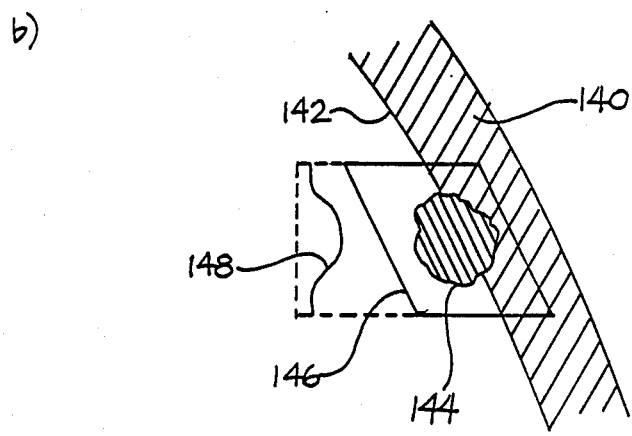

Another embodiment is employed when the rib edge defines a line whose slope, with respect to the horizontal, is greater than or equal to unity, i.e., is greater than or equal to 45°. FIG. 11 illustrates this embodiment.

FIG. 11 illustrates a rib 140 having an edge 142 approximately defining a line whose angle to the horizontal is greater than 45°. A nodule 144 is also illustrated. A cursor 146, having the configuration of a parallelogram without right angles is also illustrated. In this embodiment, one of the line pairs defining the parallelogram are substantially parallel to the line 142. The opposite pair of sides are horizontal.

In this embodiment, the pixel lines encompassed within the cursor 146 are summed in a horizontal direction. This means that there is in the FIG. 11 embodiment also no need to utilize complex reprojection techniques to sum pixel lines, the summation taking place horizontally in the image, along the direction of the pixel rows inherently defined in the display and by the system circuitry.

A profile 148 is also shown, representing the result of the summations taking place. The profile 148 is employed in a manner analogous to that discussed in connection with FIGS. 7 and 8.

Thus, utilizing the embodiments of FIGS. 10 and 11, two of the parallelogram lines defined by the cursor configuration are substantially parallel to the rib edge, while the remaining two lines are parallel to either the pixel rows or pixel columns. In these embodiments, reprojection reduces to the trivial operation of row-wise or column-wise summation.

The parallelogram configuration for the cursor affords more positional flexibility than does a rectangle, allowing one to quantify calcium in nodules or other structures that are in difficult locations.

The relevant operating principles for constructing the cursor are that:

(1) where an interfering or obscuring object defines a generally linear edge, one line pair of the parallelogram should be parallel to that edge, and (2) lines of pixel summations should extend parallel to the other line pair, irrespective of the direction of that other line pair. No other geometrical condition is essential. It is not required that other line pair be parallel to pixel rows or columns, though, as discussed above, it may sometimes be desirable to so construct the cursor.

Figure 12:
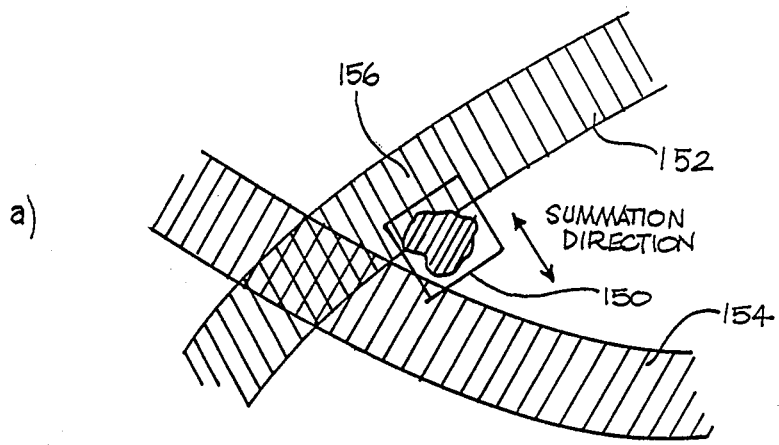

FIG. 12 shows an instance where a rectangular cursor 150 overlies two ribs 152, 154 even though a nodule 156 overlies only one rib 152. Even if the nodule were not present, the background profile, to which only the rib and background calcium contribute (analogous to that of FIG. 8) would not be a straight line. Thus, estimation of that profile from the tails of the profile analogous of that to FIG. 7, to which all of the rib, background and nodule contribute, would be inaccurate, making quantification of calcium in the nodule correspondingly inaccurate.

Figure 13:
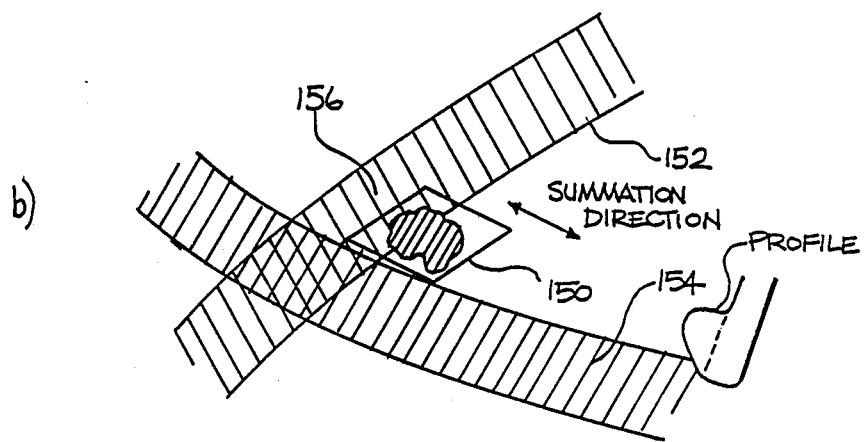

FIG. 13 indicates how the generalized parallelogram form of cursor affords the flexibility, in a situation such as FIG. 12, of structuring the cursor such that it encompasses a portion of only one rib. Calcium quantification accuracy in this instance is maintained.

As often happens in practice, FIG. 13 shows one side of the parallelogram skirting very closely to the nodule. Because of this, substantially no "tail" portion of the profile will appear corresponding to this side of the nodule. The tail from the other side of the nodule must in such instance be used (e.g. by extrapolation) to estimate the profile analogous of FIG. 8 to which only the rib and background contribute, so that it may be subtracted away. This one tail extrapolation method has been found in tests to give good results, although it is considered preferable where available to use the two tail technique in estimating the background contribution.

Figure 14:
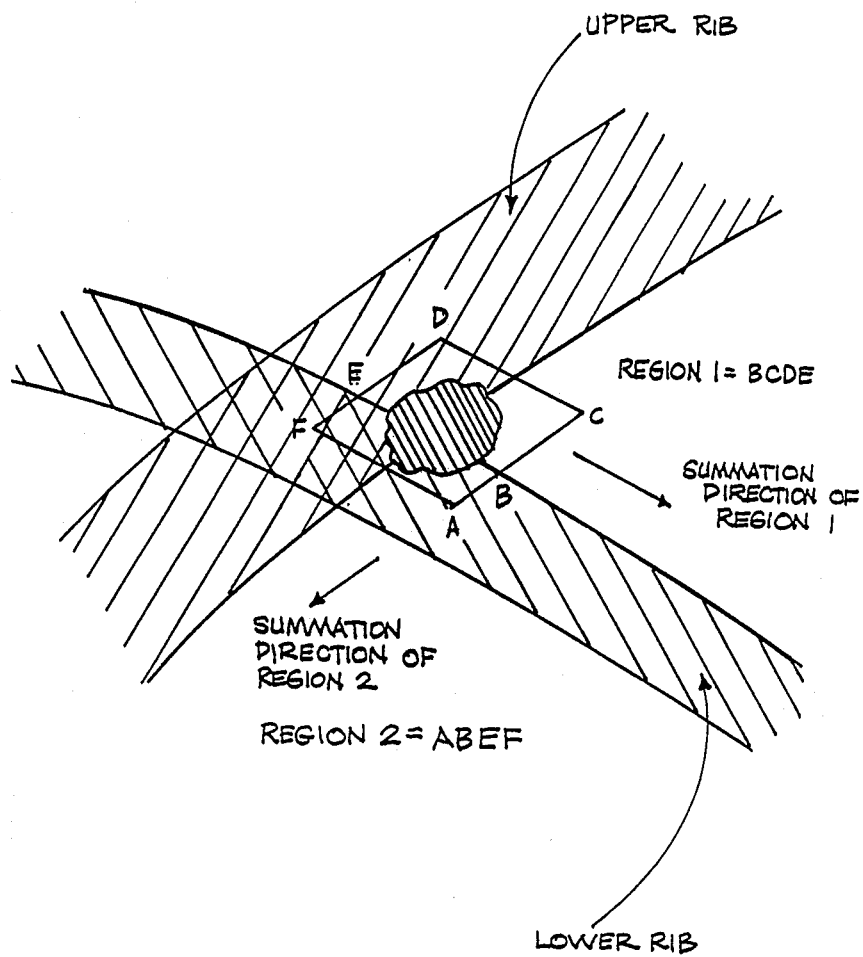

Sometimes a nodule will overlie more than one rib. Quantification even in this instance is still possible, but requires that the nodule be considered as broken-up or segmented into several contiguous regions. Refer to FIG. 14. The calcium content of each region of the nodule is calculated as described above, and the results are added to obtain the total calcium content of the nodule.

There is a subtlety involved in the segmentation technique of FIG. 14. A region 1 includes part of the nodule and part of the upper rib. Quantification of this region poses no problem, being done in a manner analogous to that discussed in connection with FIG. 13. However, a region 2, as described in FIG. 14, includes a subregion where the upper and lower ribs overlap. The sides (bases) AF and BE of the region 2 parallelogram are parallel to the edge of the lower rib, but not parallel to the edge of the upper rib. Hence, the portion of the profile contributed by only the background and the rib of region 2 is not flat, and the model upon which the quantification technique is based is not strictly correct.

Tests have shown, however, that the segmentation technique depicted in FIG. 14 works quite well when estimation of the rib/background contribution is made utilizing two "tails" of each profile. This is believed to be the case because estimation using two tails averages the tails on either side of the nodule, giving an estimated mean for the rib/background profile which is acceptably proximate the actual mean.

Generation of cursor graphics will now be discussed. A parallelogram is defined when three of its vertices are defined. An operator can define a parallelogram using the trackball of the viewing console and a point cursor (that is, a small, essentially single pixel cursor). The point cursor is moved around by using the trackball and when it is in a location judged by the operator to be appropriate for a vertex of the parallelogram, the operator in known fashion actuates the viewing console to "write" a dot (vertex) into the display overlay plane. Then the operator can move the point cursor to the next place where a vertex is desired, etc.

The operator first defines two such points which define a line segment parallel to a rib edge, as described in more detail below. These points (pixels) are appropriately called $P_1$ and $P_2$. Once $P_1$ and $P_2$ are defined, the processing unit takes their x-y coordinates and calculates the best (pixel) line connecting these points, in a manner analogous to that disclosed in the Joseph and Newman publications incorporated herein. Techniques for taking the coordinates of two points and generating a best pixel line connecting them are well known, as set forth in the above referenced articles. After the points on this line are calculated, the line is written into the display overlay plane.

Next, the operator defines a third point in such a way that the ensuing parallelogram encloses the region of interest appearing in the analog image. Once the third point $P_3$ is defined, it is a simple matter for the processing unit to calculate the fourth and final point $P_4$.

The calculation of the location of $P_4$ is accomplished in the following way: let $X_1$ and $Y_1$ be the coordinates of $P_1$, etc. Then, $$X_4 = (X_3 - X_2) + X_1$$

$$Y_4 = (Y_3 - Y_2) + Y_1$$

Once $P_1$–$P_4$ are known, the processing unit uses a known line drawing technique to write the remaining three sides of the parallelogram into the overlay plane. Let us call the base, and the side parallel to the base, (both parallel to the rib edge) both "bases" of the parallelogram, and call the other two sides "sides". Also, call the "length" of the parallelogram the length of (number of pixels in) each of the bases, and the "width" of the parallelogram the length of (number of pixels in) each of the sides. This nomenclature will be convenient in the discussion below.

After the parallelogram is completely defined and displayed, the processing unit then operates to acquire the summation profile in accordance with known technique. Pixel summations are done parallel to the sides of the parallelogram.

The technique for profile generation is now discussed. One begins with the pixel line (parallelogram side) defined between $P_1$ and $P_4$. One then adds up all the values of the pixels in this line. This represents the first "projection" (point, value, or element) of the profile. Next, one moves to the next pair of points of the respective parallelogram bases, using the line defining technique described above to define a pixel line between these points. One then adds up all the values of the pixels in this new line. This is the second "projection" of the profile. One then continues moving to successive pairs of respective base points until the other side of the parallelogram is reached, i.e., points $P_2$, $P_3$. The profile is generated in this way. This is the profile which is then "tail-subtracted" and "integrated", as described in detail in connection with FIGS. 7 et seq.

Where integration of the area under a curve is required, the integration simply amounts to summing up the profile projections after subtracting the tail background.

It will be seen, in connection with the above approach to profile generation, wherein pixel lines are approximated by reprojection, that some pixels are used more than once during the summations, and other pixels are not used at all. That is, the total number of pixels used in generating the profile is not necessarily equal to the total number of pixels contained in the parallelogram, due to the line approximation technique which is necessary, and which is discussed in connection with the incorporated publications by Joseph and Newman. Ideally, if one took the profile and summed all the values in the profile without tail background correction, one would get the same answer as summing all the pixels in the parallelogram. Since this is not true in practice, one must apply a correction factor to the result of profile integration. The correction factor is simply the ratio of the actual number of pixels in the parallelogram, including those representing the bases and sides, to the number of pixels used in generating the profile. The number of pixels N used in generating the profile is simply the length times the width of the parallelogram. The actual number of pixels in the parallelogram (A) is calculated from a formula for the area of a parallelogram:

$$A = (X_1 Y_2) + (X_2 Y_3) + (X_3 X_1) - (X_3 Y_2) - (X_2 Y_1) - (X_1 Y_3).$$

Therefore, equation (4) of the disclosure becomes:

$$B = (A/N)(K\ A_p/M^2)S \qquad (5)$$

Several of the above disclosed equations incorporate a constant K which is derived from, and which is a characteristic of, the particular attributes of the system being used. K is conveniently expressed in units of milligrams per square centimeter (mg/cm$^2$) per pixel count.

A step-wedge phantom containing steps of various known thicknesses (mg/cm$^2$) of calcium is imaged, and these thickness are plotted vs. the bone image pixel values that the thicknesses of calcium yield. The plot is a straight line with slope K.

It is to be understood that this disclosure is intended as illustrative, rather that exhaustive, of the invention. It is to be further understood that those of ordinary skill in the relevant technical field may be able to make additions or modifications to or deletions from, the embodiments described herein, without departing from the spirit or the scope of the invention as defined in the following claims:

We claim:

1. A method of evaluating the amount of a particular substance within an object of interest in a subject body, wherein the substance in said object of interest is at least partially obscured by an additional quantity of such substance, said method utilizing a digital imaging system having source and detector means for employing penetrative radiation and for generating and storing pixel values including signals corresponding to detected radiation emergent from the subject, said method comprising the steps of:

(a) actuating the source for causing penetrative radiation to pass through both the object of interest and the obscuring quantity of the substance to emerge in a pattern;

(b) detecting the emergent pattern;

(c) generating signals defining a set of pixel values related to the emergent pattern;

(d) identifying first and second portions of said pattern, whereby a first set of pixel values corresponding to said first pattern portion and a second set of pixel values corresponding to said second pattern portion are identified;

(e) combining said first set of pixel values;

(f) combining said second set of pixel values; and (g) producing a scalar representation of the difference between the resultants produced by combining said first set of pixel values and said second set of pixel values.

2. The method of claim 1, where said substance is calcium.

3. The method of claim 2, wherein: (a) said object of interest is within a lung, and (b) said obscuring substance resides in a rib.

4. The method of claim 1, wherein step (b) comprises producing an analog display image corresponding to said pattern, and step (c) comprises defining a cursor on said image whereby the cursor overlies the image portion corresponding to either of said first or second pattern portion.

5. The method of claim 4, wherein said cursor defining step comprises: defining a cursor having a rectangular configuration.

6. The method of claim 4, wherein said obscuring quantity of the substance comprises a rib, and said cursor defining step comprises: defining a cursor configured as a parallelogram and having one of its line pairs aligned approximately parallel to an edge of said rib.

7. The method of claim 6, wherein said cursor defining step comprises: defining said parallelogram shaped cursor at a location such that said rib edge passes through the region encompassed by the cursor.

8. The method of claim 1, performed in an energy subtraction mode, wherein step (a) comprises causing penetrative radiation at least two different energies to pass through the object of interest, step (b) comprises detecting emergent patterns corresponding to each of said different energies of penetrative radiation, and step (c) comprises combining the pixel values at the energies to generate material specific values to reduce the magnitude of effects on the pixel values caused by attentuation of said penetrative energy by materials in said body other than said particular substance.

9. The method of claim 1, wherein the boundaries of said first and second pattern portions enclose substantially congruent regions.

10. A method for quantifying a predetermined substance localized within a region of interest of a subject body and at least partially obscured by an additional quantity of said substance, said method utilizing a digital imaging system having means for employing penetrative radiation and for generating and storing pixel values including signals corresponding to radiation emergent from the subject, said method comprising the steps of:
(a) causing penetrative radiation to pass through a portion of the body including said region of interest and said obscuring quantity of substance and to emerge in a pattern;
(b) detecting the emergent pattern;
(c) generating signals defining a set of pixel values related to the emergent pattern;
(d) defining a set of said signals corresponding to a predetermined portion of said pattern, said pattern portion defines as a parallelogram having base and side portions and encompassing the localized region of interest and a portion of said body inside said region;
(e) separately summing pixel values corresponding to respective substantially parallel lines of said pixels within said parallelogram;
(f) producing a profile of said summations, said profile defining a first portion corresponding to pixel lines intersection said predetermined substance and a second portion corresponding to pixel lines not intersecting the predetermined substance;
(g) utilizing said second portion of said profile to estimate the contribution to said profile of said obscuring quantity of said substance located inside said region of interest;
(h) producing a representation of said summation profile less said estimated value of said contribution to the profile of said obscuring quantity of said substance; and
(i) producing a representation of the integral of the remainder of said summation profile subsequent to the performance of step (h).

11. The method of claim 10 performed in an energy subtraction mode, wherein step (a) comprises causing penetrative radiation at two different energies to pass through the object of interest, step (b) comprises detecting emergent patterns corresponding to each of said different energies of penetrative energy, and step (c) comprises combining the pixel values to reduce the magnitude of the effects on the pixel values caused by attenuation of said penetrative energy by materials in said body other than said predetermined substance.

12. The method of claim 10, wherein said summation step is conducted along lines substantially parallel to said sides of said parallelogram.

13. The method of claim 10, wherein said additional quantity of said substance resides in an interfering object defining an edge which approximates a straight line, said pixel value summation step comprising:
summing said pixels along respective lines in a direction substantially perpendicular to said edge.

14. The method of claim 10, wherein said additional material resides in an interfering object defining a substantially straight line, and wherein said parallelogram is defined with sides substantially parallel to said edge.

15. The method of claim 10, wherein said pattern portion defining step comprises defining said parallelogram as having a rectangular configuration.

16. The method of claim 10, wherein the pixels represented by said signals define a rectangular array of rows and columns of pixels, and wherein said additional quantity of said substance resides in an interfering object defining an edge approximating a straight line, said pattern portion defining step comprising:
defining said parallelogram wherein one line pair of the parallelogram is oriented parallel to one of a row and column of said pixel array.

17. A digital system for evaluating the amount of a predetermined substance in a particular localized region of interest in a subject to be examined, said system comprising:
(a) an energy source for propagating penetrative energy through said localized region of interest to emerge in a pattern;
(b) a penetrative radiation detector for detecting the emergent penetrative radiation pattern, said detector being spaced from said source for accommodating the subject therebetween;
(c) conversion means operatively associated with said detector for generating, in response to said detected emergent pattern, a first set of signals representing pixel values corresponding to a portion of the subject including at least a portion of the localized region of interest, and a second set of signals representing pixel values corresponding to a different portion of the subject not including the localized region of interest;

(d) means operatively associated with said conversion means for combining separately the pixel values represented by said respective first and second signal sets, and (e) means for comparing said respectively combined pixel values from said first and second pixel value signal sets for producing a tangible indication of a scalar which is a function of the quantity of said predetermined substance in said region of interest.

18. A method of quantifying the amount of particular substance within a first portion of a subject body, wherein the substance in said first body portion is at least partially obscured with an additional quantity of such substance within said first portion and wherein a like amount of said additional quantity is within a second portion of the body, said method utilizing a digital imaging system having means for employing penetrative radiation and for generating and storing pixel values including signals corresponding to radiation emergent from the subject, said method comprising the steps of:

(a) causing penetrative radiation to pass through at least the first and second body portions and to emerge in a pattern;

(b) detecting the emerging pattern;

(c) generating signals defining a set of pixel values representing the pattern;

(d) defining a first pattern portion at least partially encompassing the first body portion;

(e) defining a second pattern portion at least partially encompassing the second body portion;

(f) summing the pixel values corresponding to said first pattern portion to form a first sum;

(g) summing the pixel values corresponding to said second pattern portion to form a second sum; and (h) producing a scalar representation of the difference between said sums.

19. The method of claim 18, wherein said pattern portion defining steps each comprise: (a) producing an analog display image corresponding to said set of pixel values, and (b) defining a first and second cursor encompassing first and second image portions corresponding to said first and second pattern portions.

20. A digital radiographic imaging system including means for causing penetrative radiation to pass through a subject and emerge therefrom in a pattern, and for generating imaging signals representing image pixel values corresponding to said pattern, said system further comprising;

means for employing said image pixel signals for quantifying the amount of a known substance occurring in a particular object of interest in the subject wherein an additional quantity of said predetermined substance occurs within the subject at positions such that the additional quantity interferes with acquisition of data describing the object of interest, said means comprises:

(i) means for designating a first set of pixel values corresponding to a portion of said pattern at least partially including a region of interest;

(ii) designating a second set of pixel values corresponding to a second portion of said pattern different from said first portion and not including said region of interest, and (iii) comparing said first and second pixel value sets for producing a scalar indication which is a function of the quantity of said predetermined material present in said region of interest.

21. A digital radiographic imaging system including means for causing penetrative radiation to pass through a subject and emerge therefrom in a pattern, and for generating imaging signals representing image pixel values corresponding to said pattern, said system further comprising:

means for employing said image pixel signals for quantifying the amount of a known substance occurring in a particular object of interest in a subject body, wherein an additional quantity of said predetermined substance occurs within the subject at positions such that the additional quantity interferes with acquisition of data describing the object of interest, said means for quantifying comprises:

(a) means for actuating the system to produce and store first and second sets of pixel value signals representing first and second pattern portions;

(b) means for summing the first set of pixel values;

(c) means for summing the second set of pixel values, and (d) means for producing a scalar representation of the difference between sums.

22. The system of claim 21, said substance comprising calcium.

23. The system of claim 21, wherein said actuation means comprises:

(a) means for producing an analog display image corresponding to said pattern, and (b) means for defining a cursor on said image overlying the image portion corresponding to a pattern portion.

24. The system of claim 23, wherein said cursor defining means comprises means for defining a cursor configuration as a parallelogram and having one of its line pairs aligned approximately parallel to an edge of a rib.

25. The system of claim 23, wherein said cursor defining means comprises means for defining a cursor configuration as a parallelogram and having one of its line pairs aligned approximately parallel to an edge of a rib.

26. A method for quantifying the amount of a predetermined substance located within a predetermined region of a subject, said method utilizing a digital imaging system having means for employing penetrative radiation and for generating and storing pixel values including signals corresponding to radiation emergent from the subject, said method comprising the steps of:

(a) utilizing said pixel values to produce an analog image describing the internal structure of the predetermined region, and (b) utilizing said pixel signals to produce a scalar indication of the quantity of the predetermined substance located within the predetermined region of the subject.

27. A digital radiographic imaging system including means for causing penetrative radiation to pass through a subject and emerge therefrom in a pattern, and for generating imaging signals representing image pixel values corresponding to said pattern, said system further comprising:

(a) means for employing said imaging signals for quantifying the amount of a known substance occurring in a particular object of interest in the subject, wherein an additional quantity of said predetermined substance occurs within the subject at positions such that the additional quantity interferes with acquisition of data describing the object of interest, said system comprising;

(b) apparatus and circuitry for actuating the system to produce and store a set of imaging signals representing image pixel values corresponding to a pattern portion defined as a parallelogram having base and side portions and encompassing a localized region of interest including the object of interest;

(c) means for separately summing pixel values corresponding to respective substantially parallel lines of said pixels within said parallelogram;

(d) producing a profile of said summations, said profile defining a first portion corresponding to pixel lines intersecting said object of interest and a second portion corresponding to pixel lines not intersecting the object of interest;

(e) means for utilizing said second portion of said profile to estimate the contribution to said profile of said additional quantity of said substance located inside of said region of interest;

(f) means for producing a representation of said summation profile less said estimated value of said contribution to the profile of said additional quantity of said substance, and (g) means for producing a representation of the integral of the remainder of the remainder of said summation profile subsequent to the performance of step (e).

28. A system for quantifying a predetermined substance localized within a region of interest in an animal body and at least partially obscured by an additional quantity of said substance, said system comprising:

(a) means for causing penetrative radiation to pass through a portion of the body including said region of interest and said obscuring quantity of substance and to emerge in a pattern;

(b) means for detecting the emergent pattern and for generating signals defining a set of pixel values representing the pattern;

(c) means for storing said signals;

(d) means for defining a set of said signals corresponding to a predetermined portion of said pattern;

(e) means for producing and storing a set of signals representing pixel values corresponding to a predetermined portion of said pattern, the pattern portion being defined as a parallelogram having base and side portions and encompassing said region of interest and a portion of said body outside said region of interest;

(f) means for separately summing pixel values corresponding to respective substantially parallel lines of said pixels within said parallelogram;

(g) means for producing a profile of said summations, said profile defining a first portion corresponding to pixel lines intersecting said region of interest and a second portion corresponding to pixel lines not intersecting the region of interest;

(h) means for utilizing said second portion of said profile to estimate the contribution to said profile of said additional quantity of said substance located outside said region of interest;

(i) means for producing a representation of said summation profile less said estimated value of said contribution to the profile of said additional quantity of said substance, and (j) means for obtaining the integral of the area corresponding to the said first portion of said summation profile and for producing a representation of said integral of said first portion of said summation profile.

29. A digital radiographic imaging system including means for causing penetrative radiation to pass through a subject and emerge therefrom in a pattern, and for generating imaging signals representing image pixel values corresponding to said pattern, said system further comprising:

means for employing said image pixel signals for quantifying the amount of a known substance occurring in a particular object of interest in a subject body, wherein an additional quantity of said predetermined substance occurs within the subject at positions such that the additional quantity interferes with acquisition of data describing the object of interest.

30. A method for quantifying a predetermined substance included within an object in a subject body, said method utilizing a digital imaging system having source and detector means for employing penetrative radiation for generating and storing signals representing pixel values including signals corresponding to radiation emergent from the subject, said method comprising the steps of:

(a) actuating the source for causing penetrative radiation to pass through a portion of the body including the object and to emerge in a pattern;

(b) detecting the emergent pattern;

(c) generating signals defining a set of pixel values corresponding to a predetermined portion of said pattern, said pattern portion corresponding to the object and an additional portion of said body;

(d) combining pixel values corresponding to respective substantially parallel lines of said pixels within said pattern portion;

(e) producing by use of said combined signals a profile of said combinations, said profile corresponding to pixel lines overlying said object;

(f) producing by use of said profile an indication of attenuation of radiation in a part of the body not overlying said object, and (g) utilizing said profile and said indication to produce a signal indicating the quantity of said predetermined substance in said object.

31. A method for quantifying a predetermined substance in a first object within a body where the body also contains a second object containing a quantity of said substance and defining a generally linear edge, said method utilizing a digital imaging system having means for employing penetrative radiation and for generating and storing pixel values including signals corresponding to radiation emergent from the subject, said method comprising the steps of:

(a) causing penetrative radiation to pass through a portion of the body including said first and said second objects, some of said radiation passing sequentially through both said first and second objects, said radiation emerging in a pattern;

(b) detecting the emergent pattern;

(c) producing a set of pixel value signals corresponding to a predetermined portion of said detected pattern, said pattern portion being defined as a parallelogram encompassing said first object and at least part of said second object, one line pair of said parallelogram being parallel to said edge of said second object;

(d) separately summing pixel values corresponding to respective substantially parallel lines of pixels within said parallelogram, said lines of pixel summation extending substantially parallel to the other line pair of said parallelogram, irrespective of the direction of said other line pair;

(e) recording said summations, including separately recording summations corresponding to a first set of pixel lines overlying said first object and a second set of pixel lines not overlying said first object;

(f) comparing said summations to produce an indication of the quantity of said predetermined substance present in said first object.

32. The method of claim 31, wherein:

(a) said signal set producing step comprises defining said parallelogram with one line of said other line pair closely skirting said first object, and (b) said second set of pixel lines lies substantially only on one side of said first object.

33. The method of claim 31, wherein said body also contains a third object defining a generally linear edge oriented at a different angle than the linear edge of said second object, said third object also containing a quantity of said substance, said method further comprising the steps of:

(a) said penetrative radiation causing step further including passing radiation sequentially through said first, second and third objects, and (b) said parallelogram encompassing said first object, and at least a portion of each of said second and third objects, one line pair of said parallelogram being oriented substantially parallel to the edge defined by said second object, the other line pair of said parallelogram being oriented substantially parallel to the edge defined by said third object.

34. The method of claim 33, wherein said summing step comprising summing pixel lines in a first subregion of said parallelogram in a direction substantially parallel to said one line pair and also summing pixel lines in a second subregion of said parallelogram in a direction substantially parallel to said other line pair.

35. A method of quantifying the amount of a predetermined substance in an object existing within a subject body, said method utilizing a digital imaging system having means for employing penetrative radiation and for generating and storing pixel values including signals corresponding to radiation emergent from the subject, said method comprising the steps of:

(a) passing penetrative radiation through said object and through another portion of said body to emerge in a pattern;

(b) detecting the emergent pattern;

(c) dividing the emergent pattern into image pixels and assigning brightness value to each pixel as a function of attenuation of radiation detected in said emergent pattern;

(d) summing image pixel values corresponding to a part of said pattern including at least a portion of said object;

(e) summing image pixel values for another part of said detected pattern corresponding to an area not including said object, and (f) comparing the results of said summation steps.

36. A digital imaging system comprising:

(a) detector means for generating from a subject pixel values representing a pattern of radiation emergent radiation descriptive of internal subject structure;

(b) means for storing said pixel values;

(c) means associated with said detector means for producing an image of said internal subject structure in response to said pixel values, and (d) means for processing said image pixel values for producing a scalar indication of the quantity of a particular predetermined substance within a particular subject region corresponding to a selected portion of said image.

* * * * *